United States Patent [19]

Andermann

[11] Patent Number: 5,036,095
[45] Date of Patent: Jul. 30, 1991

[54] THERAPEUTIC USE OF DMDM HYDANTOIN

[76] Inventor: Guy Andermann, 2, Rond Point de l'Esplanade, F 67000 Strasbourg, France

[21] Appl. No.: 436,216

[22] Filed: Nov. 14, 1989

[51] Int. Cl.$^5$ .................... A01N 43/50; C10M 105/08
[52] U.S. Cl. .................... 514/389; 514/859; 252/51.5 A
[58] Field of Search .................... 514/389, 859

[56] References Cited

U.S. PATENT DOCUMENTS

| 3,987,184 | 10/1976 | Foelsch | 514/389 |
| 4,073,924 | 2/1978 | Sonntag | 514/389 |
| 4,073,926 | 2/1978 | Sonntag | 514/389 |
| 4,073,927 | 2/1978 | Freilich | 514/389 |
| 4,172,140 | 10/1979 | Shull et al. | 514/389 |

OTHER PUBLICATIONS

Schanno, R. J. et al.; Evaluation of 1,3-Dimethylol-5,-5-Dimethyl Hydantoin as a Cosmetic Preservative.

Primary Examiner—Stanley J. Friedman
Assistant Examiner—Theodore J. Criares
Attorney, Agent, or Firm—Rosenthal & Putterman

[57] ABSTRACT

This invention is for the use of DMDM Hydantoin as a pharmaceutical compound for the treatment of malconditions of mammalian and human skin and membranes. In particular, DMDM Hydantoin may be used to treat dermatological conditions such as acne, burns, and lacerations. DMDM Hydantoin may also be used as an aqueous spray, mouthwash and may be used to treat eye and ear infections as well as to treat mastitis in cattle.

6 Claims, No Drawings

THERAPEUTIC USE OF DMDM HYDANTOIN

BACKGROUND OF THE INVENTION

This invention relates generally to the field of pharmaceutical preparations and more particularly to pharmaceutical preparations employing DMDM Hydantoin as an active ingredient.

DESCRIPTION OF THE PRIOR ART

DMDM Hydantoin is a common name for the chemical compound 1.3-dimethylol-5, 5-dimethyl hydantoin supplied as a 55% solution and having the following structural formula:

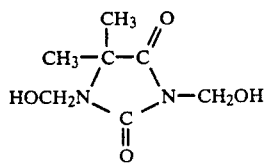

DMDM Hydantoin is a hydantoin-type condensation product. The method of its preparation is disclosed in U.S. Pat. No. 3,987,184. DMDM Hydantoin has been widely used as an antimicrobial preservative in cosmetic compositions. The properties of DMDM Hydantoin are also well known and are described by Shanno, Westlund and Foelsch, Journal of the Society of Cosmetic Chemistry, 1980, 31, 85–96 and in the "Final Report of the Safety Assessment for DMDM Hydantoin", published by the Cosmetic, Toiletry and Fragrance Association, Inc. (USA) in 1985.

As stated above, DMDM Hydantoin has found application as a preservative in a wide variety of non-therapeutic products, and literature has been published in that respect both alone and in combination with other preservatives. To this date, there has been no suggestion that DMDM could be useful beyond the field of human and animal diseases.

SUMMARY OF THE INVENTION

The general purpose of the present invention relates to the therapeutic use of DMDM Hydantoin as a pharmaceutical composition in association with carriers for topical application to mammalian skin and other membranes for use in the treatment in diseases thereof. In particular, DMDM Hydantoin has been found to be useful for the non-antibiotic chemotherapeutic treatment of humans and other mammals for which prophylactic and curative purposes, where the use of antibiotics would be undesirable.

In a preferred embodiment of this invention, DMDM Hydantoin has been found to be effective in the treatment of dermatological conditions such as acne in the form of pustular, papular or comedonic dermatitis. It is important to note that acne, as well as many other dermatological conditions irritate and inflame the skin. Therefore, any formulation for the treatment thereof must be of low irritation, even at high concentrations. It is precisely this characteristic combined with its efficacy that makes DMDM Hydantoin suitable for the treatment of acne, as well as other dermatological conditions. DMDM Hydantoin may be formulated as a cream for the treatment of acne as follows:

| | |
|---|---|
| DMDM Hydantoin | 0.5% |
| Quarternium-3 ® | 0.15%–0.30% |
| Polyoxyethylen alkylether | 6.0% |
| Carbopol | 1.5%–3.0% |
| Trithanolamine | 0.65% |
| Titanium Dioxide | 1.0% |
| Water | to 100.0% |

In the above noted example, all percentages given are calculated by weight and are based on the total weight of the formulation.

DETAILED DESCRIPTION OF THE PRESENT INVENTION

In the pharmaceutical field, DMDM Hydantoin has been found to be particularly effective in the treatment of malconditions of the skin, including acne, burns, herpes, vulgaris, ulcers and other dermatological malconditions. DMDM Hydantoin may also be useful in the treatment of burns, skin grafts and skin lacerations. Furthermore, DMDM Hydantoin may also be used to treat the eyes and ears of mammals, as well as in mouth washes for pre and post dental treatment.

In the veterinary field, DMDM Hydantoin may be particularly effective in the treatment of mastitis, primarily in cattle.

DMDM Hydantoin may be formulated for human and veterinary use in a variety of forms depending on the particular intended use. Examples of the types of formulations suitable for the treatment of human diseases include various preparations for application to the human skin, for example, creams, lotions, gels, ointments, aerosol sprays, as well as preparations for external application to the eyes and ears of humans, such as eye-drops, eye and ear ointments, mouthwashes and pre-operative swabs.

Examples of formulations suitable for the treatment of mammals include compositions for systemic and external application to cattle udders, for instance in the form of a gel or in the form of a solution, compositions for external application to the eyes and ears of mammals, for example, as eye-drops, ear-drops, and ointments.

Formulations with DMDM Hydantoin for the therapeutic treatment of mammals may contain DMDM Hydantoin concentrations of anything up to approximately 30%, depending on the intended use of the particular formulation. Advantageously, concentrations of about 0.10 percent to 30 percent by weight may be used, but concentrations from 0.5 percent to 10 percent by weight are preferred, based on the total weight of the formulation.

The compositions of DMDM Hydantoin according to the disclosure of the present invention may contain various ingredients such as carriers, solvents, diluents, buffers, thickening agents, dispersants, emulsifiers, propellants and other conventional excipients. The choice of auxiliaries for any particular formulation will of course depend on the type of formulation, whether the formulation is intended for internal or external application, or whether its intended use is animal or human.

MODES OF OPERATION

A. Dermatological Applications

DMDM Hydantoin is useful in the treatment of dermatological diseases and has been found to be particularly effective in the treatment of acne in the form of pustular, papular or comedonic dermatitis, associated or not with pathogens of the Corynebacterium acnes group, or the Staphylococcus group. Effective treatment of the foregoing conditions can be difficult as it is necessary to use a substance which is effective against inflammatory and noninflammatory lesions, and which is itself of low irritation so as not to irritate the skin further DMDM Hydantoin is effective against the pathogens mentioned above as it has the ability to reduce the number of papules, pustules, and comedones in acne patients, and has the advantage to be of low irritation and toxicity. These properties also mean that it can be used in concentrations high enough to combat acute and chronic acne conditions.

EXAMPLE 1

Cream for dermatological conditions

All percentages given are calculated by weight and are based on total weight of the formulation.

| DMDM Hydantoin | 1.0% |
|---|---|
| Cetostearyl alcohol | 4.0%–10.0% |
| Sodium laurylsulfate | 0.1%–1.0% |
| Methyl hydroxybenzoate | 0.05%–0.15% |
| Glycerol | 1.0% |
| Water | to 100.0% |

The above formulation may be modified to include DMDM Hydantoin in concentrations ranging from about 0.1% to about 5.0%.

EXAMPLE 2

Cream for the treatment of acne

All percentages given are calculated by weight and are based on the total weight of the formulation.

| DMDM Hydantoin | 0.5% |
|---|---|
| Quarternium-3 ® | 0.010%–0.04% |
| Polyoxyethylene alkylether | 3.0%–10.0% |
| Carbopol | 1.0%–5.0% |
| Triethanolamine | 0.35%–1.5% |
| Titanium Dioxide | 0.30%–2.5% |
| Imidurea | 0.3%–0.6% |
| Purified Water | to 100.0% |

The above formulation may be modified to include DMDM Hydantoin in concentrations ranging from about 0.1% to about 5.0%.

DMDM Hydantoin may also be effective against ammoniacal dermatitis, ichthyosis, as well as in the treatment of tissues damaged by burns, lacerations, and the like in mammals. Tissues that have been damaged by burns or lacerations are extremely sensitive, and any substance used in the treatment thereof must, therefore, be of low irritation, even at high concentrations. In addition, Pseudomonas, a pathogen which is difficult to control, even with the use of antibiotics, is often present in burns and lacerations. On the other hand, most non-antibiotic agents are to irritating to be used on damaged tissues. DMDM Hydantoin is, however, very suitable for this purpose because of its effectiveness against Pseudomonas combined with its low irritation potential. Moreover, because of its water solubility it can be used in aqueous medium, which is compatible with tissue and tissue fluids.

EXAMPLE 3

Therapeutic treatment of injured skin

All percentages given are calculated by weight and are based on total weight of the formulation.

DMDM Hydantoin in concentrations of from 0.1% to 20%, preferably from 0.5% to 10%, especially about 1%.

The DMDM Hydantoin is incorporated into a cream, gel, ointment or aqueous or non-aqueous spray, depending on the particular application.

B. Ophthalmologic And Otologic Applications

EXAMPLE 4

Eye and Ear Drops

All percentages given are calculated by weight and are based on total weight of the formulation.

DMDM Hydantoin may also be used in the treatment of external infections of the eye and its adnexa and ear infections in both humans and animals. For this purpose it may be formulated as an eye or ear drop solution or as an ointment, advantageously containing DMDM Hydantoin in an amount of from 0.10% to 2.0%, especially about 0.50%.

| DMDM Hydantoin | 0.30% |
|---|---|
| Disodium Phosphate | 0.25% |
| Monosodium Phosphate | 0.17% |
| Sodium Chloride | 0.70% |
| Benzalkonium Chloride | 0.01% |
| Water | to 100.0% |

The above example may be modified to include DMDM Hydantoin in concentrations ranging from about 0.1% to about 1.0%. DMDM Hydantoin may also be included as a key ingredient in soaps, as well as water based and non-water based sprays for acne treatments.

C. Mouthwash

DMDM Hydantoin may also be used as a mouthwash treatment against gingivitis and periodontitis.

EXAMPLE 5

Mouthwash

All percentages given are calculated by weight and are based on the total weight of the formulation.

| DMDM Hydantoin | 1.0% |
|---|---|
| Aspartam | 0.40%–0.80% |
| Tween 80 | 1.0% |
| Flavoring agent | 2.0% |
| Sodium Carboxymethylcellulose | 1.5%–4.0% |
| Ethyl Alcohol | 5.0%–11.0% |
| Water | to 100.0% |

The above example may be modified to include DMDM Hydantoin in concentrations ranging from about 0.5% to about 5.0%.

D. Veterinary Applications

DMDM Hydantoin may also be used as an intramammary product, especially for the treatment of mastitis in cattle. The udder tissue of cattle provides a favorable breeding ground for a wide variety of both gram negative and gram positive pathogens. The udder tissue is very sensitive, and it is, therefore, important that any formulation used in the treatment of the udder, should, therefore, have a low potential for the irritation thereof.

Intramammary treatment is traditionally carried out using antibiotics but their prolonged use can cause problems of the pathogens developing resistance to the antibiotics used. Moreover, the use of antibiotics on lactating cows can create public health problems.

Intramammary products based on DMDM Hydantoin, can be used for the non-antibiotic chemotherapeutic treatment of mastitis without many of the disadvantages associated with the use of antibiotics. DMDM Hydantoin has been found to have a bactericidal activity against many of the pathogens associated with mastitis and it could, therefore, prove to be effective in overcoming situations where the disease has become endemic.

DMDM Hydantoin also has several advantages rendering it very suitable for this purpose: it has a very low degree of irritation in the udder, it is associated with very low systemic toxicity which means that it ca be used without danger to human consumers of milk from the treated cows. Since DMDM Hydantoin is water soluble, it is, therefore, effective when used in a medium such as milk as it is not inhibited by the presence of milk proteins. As an auxiliary use, DMDM Hydantoin may also be used an aqueous solution for use as a udder wash and for washing teat tips.

EXAMPLE 6

Formulation for intramammary use in lactating cows

All percentages given are calculated by weight and are based on total weight of the formulation.

| DMDM Hydantoin | 0.50% |
| Glycerol | 23.0% |
| Methyl hydroxybenzoate | 0.70%–0.15% |
| Hydroxyethylcellulose | 1.0%–5.0% |
| Water | to 100.0% |

The above example may be modified to include DMDM Hydantoin in concentrations ranging from about 0.10% to about 3.0%.

A further veterinary application for DMDM Hydantoin is the treatment of uterine infections, especially acute endometritis. This disease can occur in most mammals, especially horses. It is caused by the presence of pathogens in the uterus, which have been found to be vulnerable to DMDM Hydantoin. Drugs intended for use in uterine infusions need to be water-soluble, have low systemic toxicity, low irritation and be effective in the biological environment of the uterus. DMDM Hydantoin meets all these criteria, and can be incorporated into uterine compositions in relatively high concentration of from 1.0% to 10%, preferably, from 2–5%.

In many applications, DMDM Hydantoin is advantageously used in conjunction with Imidurea or other compositions having a potentiating effect.

The foregoing embodiments and examples are to be considered illustrative, rather than restrictive of the invention, and those modifications which come within the meaning and range of equivalence of the claims are to be included therein.

That which is claimed is:

1. A method for the treatment of acne in humans comprising the topical administration to said human of effective amount of DMDM Hydantoin in association with a topical pharmaceutical carrier, DMDM Hydantoin is provided in concentrations ranging from about 0.10% to about 5.0% by weight of the composition.

2. A method for the treatment of acne in humans comprising the topical administration to said human of DMDM Hydantoin in concentrations ranging from about 0.5% to about 2.5% Quarternium - 3® in concentrations ranging from about 0.10% to about 0.04%, Polyoxyethylene alkylether in concentrations ranging from about 3.0% to about 10.0%, Carbopol in concentrations ranging from about 1.0% to about 5.0%, Triethanolamine in concentrations ranging from about 0.35% to about 1.5%, Titanium Dioxide in concentrations ranging from about 0.3% to about 2.5% and Imidurea in concentrations ranging from about 0.3% to about 0.6%.

3. A method for the treatment of ichthyosis in humans comprising the topical administration to said human of an effective amount of DMDM Hydantoin in association with a pharmaceutical carrier, DMDM Hydantoin is provided in concentrations ranging from about 0.10% to about 5.0% by weight of the composition.

4. The method for the treatment of ichthyosis in humans according to claim 3 further including cetostearyl alcohol in concentrations ranging from about 4.0% to about 10%, Sodium Laurylsulfate inconcentrations ranging from about 0.1% to about 1.0%, Methyl Hydroxybenzoate in concentrations ranging from about 0.05% to about 0.15%, and Glycerol in concentrations of about 1.0%.

5. A method for the treatment of ammoniacal dermatitis in humans comprising the topical administration to said human of an effective amount of DMDM Hydantoin in association with a topical pharmaceutical carrier, DMDM Hydantoin is provided in concentrations ranging from about 0.10% to 5.0% by weight of the composition.

6. The method for the treatment of ammoniacal dermatitis according to claim 5 further including cetostearyl alcohol in concentrations ranging from about 4.0% to about 10%, Sodium Laurylsulfate in concentrations ranging from about 0.1% to about 1.0%, Methyl Hydroxybenzoate in concentrations ranging from about 0.05% to about 0.15%, and Glycerol in concentrations of about 1.0%.

* * * * *